United States Patent [19]

Ingendoh et al.

[11] Patent Number: 4,585,873
[45] Date of Patent: Apr. 29, 1986

[54] NOVEL HYPOTENSIVE IMIDAZOTHIADIAZOLEALKENECARBOXAMIDES

[75] Inventors: Axel Ingendoh, Velbert; Horst Meyer, Wuppertal; Bernward Garthoff, Hilden, all of Fed. Rep. of Germany

[73] Assignee: Bayer Aktiengesellschaft, Leverkusen, Fed. Rep. of Germany

[21] Appl. No.: 468,737

[22] Filed: Feb. 22, 1983

[30] Foreign Application Priority Data

Mar. 9, 1982 [DE] Fed. Rep. of Germany ....... 3208437

[51] Int. Cl.⁴ ................. A61K 31/425; C07D 277/00; C07D 513/04; C07D 513/22
[52] U.S. Cl. .................... 548/130; 548/126; 548/136
[58] Field of Search ................ 548/126, 138, 130

[56] References Cited

U.S. PATENT DOCUMENTS 4,444,770  4/1984  Meyer I, et al. ............... 548/126 X

FOREIGN PATENT DOCUMENTS 0041215  12/1981  European Pat. Off. ........... 548/126
47-47388  11/1972  Japan ................... 548/138

*Primary Examiner*—Floyd D. Higel
*Attorney, Agent, or Firm*—Sprung, Horn, Kramer & Woods

[57] ABSTRACT

Imidazothiadiazolealkenecarboxamides of the formula

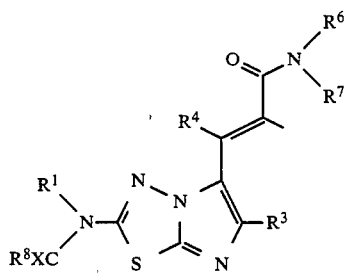

in which
$R^1$ is hydrogen, aryl, substituted aryl or a cyclic or aliphatic hydrocarbon radical which is optionally interrupted by O, S, N, N-alkyl, N-aryl or N-aralkyl and which is optionally substituted,
$R^8$ having the meaning indicated for $R^1$, and
X representing oxygen, sulphur or the radical $NR^9R^{10}$,
the other radicals having various definitions, and acid addition salts thereof, exhibit hypotensive activity.

8 Claims, No Drawings

NOVEL HYPOTENSIVE IMIDAZOTHIADIAZOLEALKENECARBOXAMIDES

The present invention relates to new imidazothiadiazolealkenecarboxamides, various processes for their preparation, new intermediate products, which are employed in their preparation, and their use in medicaments, in particular in antihypertensive, diuretic and uricosuric agents.

It has already been disclosed that certain imidazothiadiazoles have biological effects, in particular antithrombotic and antimicrobial properties (compare U.S. Specification Ser. No. 263,400 filed May 13, 1981, now U.S. Pat. No. 4,444,770.

Furthermore, it has been disclosed that certain imidazothiadiazoles and imidazothiazolesulphonamides have cerebral effects (J. med. Chem., 1980, 117, IC. Barnisch et al.).

Mention has likewise already been made of the antihypertensive, diuretic and uricosuric effect of other imidazoalkenecarboxamides (DE-OS [German Published Specification] 3,043,158).

The invention relates to new imidazothiadiazolealkenecarboxamides of the general formula (I)

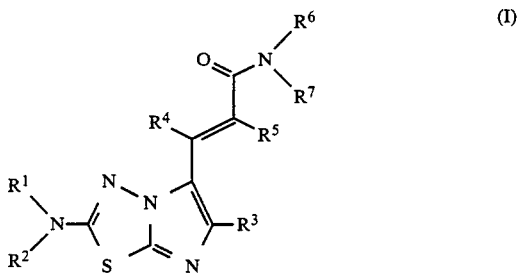

in which
$R^1$ denotes hydrogen, aryl, substituted aryl or a straight-chain or cyclic, saturated or unsaturated aliphatic hydrocarbon radical, which is optionally interrupted by O, S, N, N-alkyl, N-aryl or N-aralkyl, and which is optionally substituted by hydroxyl, alkoxy, alkyl, trifluoromethyl, halogen, phenyl, alkoxycarbonyl or dialkylamino, the two alkyl radicals together with the nitrogen atom optionally forming a 5 to 7-membered ring, which optionally contains a heteroatom from the group comprising O, S, NH or N-alkyl and these aforementioned alkyl and phenyl radicals in turn optionally being substituted by halogen, trifluoromethyl, alkyl, aryl, aralkyl, alkoxy, alkylmercapto or $SO_2$-alkyl, $R^2$ represents hydrogen, or represents the radical $CXR^8$, $R^8$ having the meaning indicated for $R^1$ and being identical to or different from $R^1$, and X representing oxygen, sulphur or the radical $NR^9R^{10}$, $R^9$ and $R^{10}$ being identical or different and each having the meanings of $R^1$ and being identical to or different from $R^1$; or represents the radical $SO_nR^{11}$, n denoting 1 or 2 and $R^{11}$ having the meaning indicated for $R^1$ and being identical to or different from $R^1$, or $R^1$ and $R^2$ together represent a group of the general formula $=C(R^{12})(Y-R^{13})$, Y representing oxygen, sulphur, NH or N-alkyl, and $R^{12}$ and $R^{13}$ each having the meaning indicated for $R^1$, being identical to or different from one another and $R^1$, and optionally together forming, with inclusion of $=C-Y$, a 5 to 7-membered ring, which optionally contains a heteroatom from the group comprising O, S, NH or N-alkyl, $R^3$ has the meaning indicated for $R^1$ and is identical to or different from $R^1$, or represents furyl, phenyl, thienyl, pyrimidyl, pyrazinyl, quinolinyl, isoquinolinyl, or pyridyl, the rings optionally being substituted by 1, 2 or 3 identical or different substituents from the group comprising alkyl, aryl, alkoxy, halogen, nitro, trifluoromethyl, $SO_n$-alkyl (n=0, 1 or 2) or $NR^9R^{10}$, $R^9$ and $R^{10}$ having the meaning indicated above, $R^4$ represents hydrogen, trifluoromethyl or alkyl, $R^5$ represents hydrogen, alkyl, cyano, halogen, nitro, $SO_n$-alkyl (n=0, 1 or 2) or $CXR^8$, X and $R^8$ having the meaning indicated above, and $R^6$ and $R^7$ each have the meaning indicated for $R^1$ and are identical to or different from $R^1$ or, together with the nitrogen atom, form a 3 to 8-membered saturated or unsaturated ring, which optionally contains 1 or 2 further heteroatoms from the group comprising oxygen, sulphur or nitrogen, the nitrogen optionally being substituted by hydrogen, alkyl, aryl or aralkyl, and this 3 to 8-membered ring optionally being substituted by 1, 2, 3 or 4 identical or different substituents from the group comprising alkyl, aryl, aralkyl, halogen, alkoxycarbonyl, hydroxyalkyl, alkoxyalkyl, alkoxy or trifluoromethyl, or it being possible for this ring to be condensed with an optionally substituted aromatic ring, and their stereoisomeric forms of the various enantiomers, diastereomers and E/Z isomers and their pharmaceutically acceptable acid addition salts.

The preparation of the imidazothiadiazolealkenecarboxamides of the general formula (I) is carried out by (a) reacting carbonyl compounds of the general formula (II)

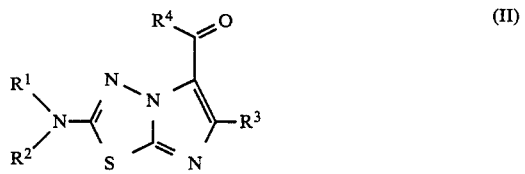

in which
$R^1$ to $R^4$ have the meaning indicated above, with phosphonate compounds of the general formula (III)

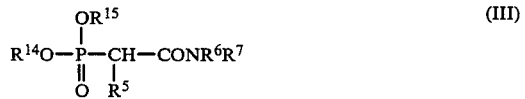

in which
$R^5$ to $R^7$ have the meaning indicated above, and
$R^{14}$ and $R^{15}$ represent optionally substituted alkyl or aralkyl, in the presence of strong bases and in inert organic solvents at temperatures between $-20°$ and $110°$ C., in the case where $R^8=CH_3$ and $X=O$, alkenecarboxamides of the general formula (I) with $R^2=H$ being obtained, or (b) reacting alkenecarboxamides of the general formula (I), in which $R^1$ to $R^7$ have the meaning indicated above and $R^2$=hydrogen, with suitable acylating agents of the general formula (IV)

$$R^{2'}-Cl \qquad (IV)$$

in which $R^{2'}$ has the meaning indicated above for $R^2$, but does not denote hydrogen, in inert organic solvents, optionally in the presence of an organic base, or (c) reacting carbonyl compounds of the general formula (II) with acetamide derivatives of the general formula (V)

$$R^5-CH_2-CONR^6R^7 \qquad (V)$$

in which $R^5$, $R^6$ and $R^7$ have the meaning indicated above, in the presence of acid or basic catalysts and optionally in the presence of inert organic solvents at temperatures between 20° and 200° C., or (d) converting alkenecarboxylic acids of the general formula (VI)

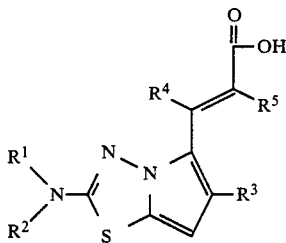

in which $R^1$ to $R^5$ have the meaning indicated above, with amines of the general formula (VII)

$$HNR^6R^7 \qquad (VII)$$

in which $R^6$ and $R^7$ have the meaning indicated above, into amides, optionally after activation of the carboxyl group via the corresponding acid chloride for example (by thionyl chloride) in a customary manner in organic inert solvents at temperatures between 20° and 150° C.

Depending on the choice of starting substances, the compounds according to the invention can exist in stereoisomeric forms, which are related to one another either as image and mirror image (enantiomers) or which are not related as image and mirror image (diastereomers). The present invention relates both to the antipodes and also to the racemates and the mixtures of diastereomers. The racemates can be separated, as can the diastereomers, in a known manner into the pure stereoisomers (compare E. L. Eliel, Stereochemistry of Carbon Compounds, McGraw Hill 1962).

Furthermore, the E/Z isomers possible due to the double bond in the side chain, which can be prepared by known processes or which can be converted into one another by known processes, are claimed. An example of a known process which may be mentioned is irradiation with UV rays.

The carbonyl compounds of the general formula (II), which can be employed as starting compounds, have not hitherto been disclosed, but they can be prepared in an analogous manner by known methods from imidazothiadiazoles of the general formula (VIII)

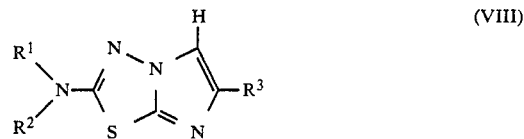

in which $R^1$ to $R^3$ have the meaning indicated above, by reacting them with dimethylformamide in the presence of phosphorus oxychloride at temperatures of 20° C.-170° C., (compare, for example, L. Pentimalli et al., Boll. Sci. Fac. Chim. Ind. Bologna 23, 181 (1965); C.A. 63, 17848 e (1965), D. Bower et al., J. Chem. Soc. 1955, 2834, A. Hetzheim et al., Chem. Ber. 103, 3533 (1970), H. Beyer et al., Z. Chem. 2, 152 (1962) and S. Kano, Yagukagu Zasski 92, 935 (1972)).

The alkenecarboxylic acids of the general formula (VI), which can be employed as starting compounds, are also new. They can be prepared by known methods by (a) reacting carbonyl compounds of the general formula (II), in which $R^1$ to $R^4$ have the meaning indicated above, with phosphonate compounds of the general formula (IX)

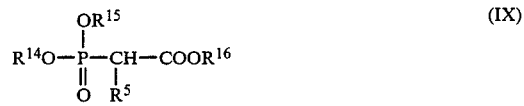

in which $R^5$, $R^{14}$ and $R^{15}$ have the meaning indicated above, and $R^{16}$ represents H, trialkylsilyl or triarylsilyl or a radical of the same meaning as $R^{14}$, in the presence of strong bases in inert organic solvents, to give the alkenecarboxylic acid derivatives, and then hydrolyzing these with acids or alkalis to give the free carboxylic acids (compare W. S. Wadsworth et al., JACS 83, 1733 (1961)), or (b) reacting carbonyl compounds of the general formula (II), in which $R^1$ to $R^3$ have the meaning indicated above, $R^4$ equals hydrogen (aldehydes), with malonic acids of the general formula $$R^5-CH(COOH)_2$$

in which $R^5$ has the meaning indicated above, or with Meldrum's acid in the presence of inert organic solvents, optionally in the presence of condensing agents (compare G. Jones, Org. Reactions, Vol. 15, pages 204 et seq.).

The imidazothiadiazoles of the general formula (VIII), which can be employed as starting compounds, are known or can be obtained, for example, by reaction of 2-bromo-5-amino-1,3,4-thiadiazole with α-halogenoketones of the general formula Y—CH$_2$—CO—$R^3$, $R^3$ having the meaning indicated above and Y representing Cl, Br or I, in organic solvents and then treating with an excess of amines of the general formula H$_2$N—$R^1$, followed by a reaction with acylating agents of the general formula $R^8CXCl$, $R^1$, $R^8$ and X having the meaning indicated above.

Unless expressly indicated otherwise, in the present application, aryl represents an aromatic hydrocarbon radical having 6 to 14 C atoms, in particular phenyl or naphthyl.

The aliphatic hydrocarbon radical represents a straight-chain, branched, cyclic, saturated or unsaturated hydrocarbon radical having up to 12 C atoms, in particular having up to 6 C atoms.

Alkyl represents a saturated, straight-chain, branched or cyclic alkyl radical having up to 10 C atoms, in particular having up to 6 C atoms.

Aralkyl preferably contains an alkylene group having 1 to 4 C atoms, which is substituted by phenyl or naphthyl.

Alkoxy preferably represents an alkoxy radical having 1 to 12 C atoms, in particular having 1 to 6 C atoms, which can be straight-chain or branched.

Halogen preferably represents fluorine, chlorine or bromine.

The present invention preferably relates to compounds of the general formula (I), in which $R^1$ represents hydrogen or phenyl, which is optionally substituted by halogen, trifluoromethyl, alkyl, alkoxy, alkylmercapto, alkylamino, each having 1 to 4 carbon atoms in the alkyl and alkoxy radicals, or by amino, or $R^1$ represents a straight-chain or cyclic, saturated or unsaturated aliphatic hydrocarbon radical having up to 12 carbon atoms, in particular having up to 6 carbon atoms, which is optionally interrupted once or twice by O, N, NH, N-alkyl (1–4 C atoms), N-phenyl or N-benzyl, and is optionally substituted by hydroxyl, alkyl, (1–4 C atoms), trifluoromethyl, halogen, phenyl or alkoxycarbonyl having up to 5 C atoms or by a dialkylamino radical, the two alkyl radicals each containing 1 to 4 carbon atoms or optionally forming with the nitrogen atom a 5 to 7-membered ring, which optionally contains a heteroatom from the group comprising O, NH or N-alkyl (1–4 C atoms), and which is optionally substituted by halogen or alkyl having 1 to 4 C atoms, $R^2$ represents hydrogen or represents the radical $CXR^8$, $R^8$ having the meaning indicated for $R^1$ and being identical to or different from this, and X representing oxygen, sulphur or the radical $NR^9R^{10}$, $R^9$ and $R^{10}$ being identical or different and representing hydrogen, phenyl, benzyl or alkyl having 1 to 6 carbon atoms, the alkyl and phenyl radicals optionally being substituted by halogen or alkoxy having 1–4 carbon atoms; or represents the radical $SO_nR^{11}$, n denoting 1 or 2 and $R^{11}$ having the meaning indicated for $R^1$ and being identical to or different from $R^1$, or $R^1$ and $R^2$ together represent a group of the general formula $=C(R^{12})(Y-R^{13})$, Y representing oxygen, sulphur, NH or N-alkyl having 1 to 4 C atoms and $R^{12}$ and $R^{13}$ each being identical or different and having the meaning indicated for $R^1$ and being identical to or different from $R^1$ and optionally together forming, with inclusion of =C—Y, a 5 to 7-membered ring, which optionally contains a heteroatom from the group comprising oxygen, sulphur, NH or N-alkyl having 1 to 4 C atoms, $R^3$ has the meaning indicated for $R^1$ and is identical to or different from $R^1$ or represents furyl, thienyl, pyrimidyl or pyridyl, the rings optionally being substituted by 1, 2 or 3 identical or different substituents from the group comprising halogen, nitro, trifluoromethyl, phenyl, alkyl, alkoxy, dialkylamino, or $SO_n$-alkyl (n=0, 1 or 2), the alkyl and alkoxy radicals mentioned each containing 1–4 carbon atoms, $R^4$ represents hydrogen, trifluoromethyl or alkyl, $R^5$ represents hydrogen, cyano, halogen, nitro, alkyl, $SO_n$-alkyl or $CXR^8$, the alkyl radicals mentioned containing 1–4 carbon atoms and n, X and $R^8$ having the meaning indicated above, and $R^6$ and $R^7$ each have the meaning indicated for $R^1$ and are identical to or different from $R^1$ or, together with the nitrogen atom, form a 5 to 7-membered saturated or unsaturated ring, which optionally contains 1 or 2 further heteroatoms from the group comprising oxygen, sulphur or nitrogen, the nitrogen optionally being substituted by hydrogen, alkyl having 1–4 carbon atoms, phenyl or benzyl and this 5 to 7-membered ring optionally being substituted by 1, 2 or 3 identical or different substituents from the group comprising halogen, trifluoromethyl, phenyl, benzyl, alkyl, alkoxy, alkoxyalkyl, hydroxyalkyl or alkoxycarbonyl, the alkyl and alkoxy radicals mentioned each containing 1–4 C atoms, or it being possible for this 5 to 7-membered ring optionally to be condensed with an aromatic ring having 6–10 carbon atoms, which in turn can be substituted by halogen, trifluoromethyl, nitroalkyl or alkoxy each having 1–4 C atoms, and their stereoisomeric forms and their pharmaceutically acceptable acid addition salts.

Compounds of the general formula (I) are particularly emphasized in which $R^1$ represents hydrogen, phenyl or a straight-chain branched or cyclic saturated or unsaturated hydrocarbon radical having up to 6 carbon atoms, which is optionally interrupted once by oxygen, NH, N-alkyl having 1–4 C atoms or N-benzyl and which is optionally substituted by halogen, $R^2$ represents hydrogen or the radical $CXR^8$, $R^8$ having the meaning indicated for $R^1$ (identical to or different from) and X representing oxygen or the radical $NR^9R^{10}$, $R^9$ and $R^{10}$ being identical or different and each having the meaning indicated for $R^1$, or $R^1$ and $R^2$ together represent a group of the general formula $=C(R^{12})(Y-R^{13})$, Y representing the radical N-alkyl having 1 to 4 C atoms and $R^{12}$ and $R^{13}$ being identical or different and each having the meaning indicated for $R^1$ and being identical to or different from $R^1$, $R^3$ has the meaning indicated for $R^1$ and is identical to or different from $R^1$ or represents phenyl, furyl, thienyl, pyrimidyl or pyridyl, the rings optionally being substituted by one or two identical or different substituents from the group comprising halogen, nitro, trifluoromethyl, phenyl, alkyl, alkoxy, dialkylamino or $SO_n$-alkyl (n=0 or 2), the alkyl and alkoxy radicals mentioned each containing 1 to 4 carbon atoms, $R^4$ and $R^5$ are identical or different and represent hydrogen or alkyl having 1–4 carbon atoms and $R^6$ and $R^7$ have the meaning indicated for $R^1$ and are identical to or different from $R^1$ or together with the nitrogen atom form a 5 to 7-membered ring, which is optionally interrupted by one oxygen or nitrogen atom, the nitrogen optionally being substituted by hydrogen, alkyl having 1–4 carbon atoms or benzyl and this 5 to 7-membered ring optionally being substituted by one or two identical or different substituents from the group comprising halogen, benzyl, trifluoromethyl, alkyl or alkoxy each having 1–4 carbon atoms, or it being possible for this ring optionally to be condensed with an aromatic ring having 6 or 10 C atoms, and their stereoisomeric forms of the various enantiomers, diastereomers and Z/E isomers and their pharmaceutically acceptable acid addition salts.

The present invention also relates to the carbonyl compounds of the general formula (II) and the alkenecarboxylic acids of the general formula (VI), which can be used as intermediate products, and processes for their preparation.

The new compounds according to the invention are surprisingly distinguished by strong biological effects. In particular, they have pronounced diuretic and saluretic effects and can thus be used as diuretics, saluretics and antihypertensive agents. In animal experiments on mice, rats and dogs, it emerges that the compounds according to the invention, on oral administration at doses as low as less than 10 mg/kg, have a pronounced diuretic and saluretic effect while at the same time, the tolerance is good. These advantageous properties could not be expected from knowledge of the state of the art.

The surprising and advantageous effects of the compounds according to the invention can be demonstrated by the following test methods:

(A) ANTIHYPERTENSIVE EFFECT ON RATS

The effect on the blood pressure is found on Goldblatt high blood pressure rats by the method of Breuninger, H.: Methoden zur unblutigen Messung des Blutdruckes an Kleintieren [Non-invasive Methods for Measuring the Blood Pressure in Small Animals], Arzneimittelforsch. 6, 222–225 (1965).

(B) DIURETIC EFFECT ON RATS

Fasting male rats weighing 150 to 250 g (SPF, Wistar, n=4 pairs each) are treated by gavage with 10 ml/kg p.o. of Tylose suspension (0.5%) as controls or with 100 mg/kg p.o. of trial substance in 10 ml/kg p.o. of Tylose suspension. The animals are placed in metabolism cages and the excretion of urine and electrolytes over 6 hours are determined ($Na^+$ and $K^+$ determination: IL flame photometer).

(C) DIURETIC EFFECT ON DOGS

The bladder of fasting, conscious female Beagle dogs is catheterized and the excretion of urine and electrolytes over 180 minutes is determined (in fractions of 30 minutes each). During this period, the animals receive via intravenous drip an electrolyte solution and, at the start of the experiment, the test substance administered orally in 1 ml/kg of Tylose suspension (0.5%). The urine is analyzed for $Na^+$, $K^+$, chlorine, bicarbonate and pH.

(D) DIURETIC EFFECT ON MICE

Fasting male SPF mice weighing 20 to 25 g (n=6×3 animals per cage) receive 100 ml/kg of Tylose suspension (0.5%) as controls or 100 mg/kg of test substance in Tylose suspension, administered orally. The excretion of urine, $Na^+$ and $K^+$ and of uric acid over 2 and 4 hours is determined in metabolism cages.

(E) PHENOL RED RETENTION TEST ON RATS

In order to detect the uricosuric effect, the action of compounds according to the invention on the level of phenol red in the blood is demonstrated on conscious, fasting male rats (SPF-Wistar, weight 180 to 250 g). Using the method of Kreppel, E. (Med. exp. 1 (1959), 285–289), 8 animals in each case receive 75 mg/kg of phenol red intraperitoneally in 5 ml/kg of saline, having had administered 30 minutes previously either 10 mg/kg of Tylose suspension (0.5%) as controls or 100 mg/kg of test substance in Tylose suspension. Plasma is obtained by puncture of the retroorbital venous plexus 30, 60 and 120 minutes after administration of phenol red or 60, 90 and 150 minutes after administration of a substance, NaOH is added and the extinction at 546 nm is determined in a photometer (Eppendorf).

A potential uricosuric effect is present when the extinction values are significantly higher than in the control group.

The new compounds according to the invention are substances which can be used as medicaments. On oral or parenteral use, they bring about an increase in the excretion of water and salt and can thus serve to treat oedematous and hypertensive states and to flood out toxic substances.

Furthermore, the compounds can be employed on acute renal failure. In particular, they also show an advantageous uricosuric effect.

The new compounds can be converted in a known manner into the customary formulations, such as tablets, capsules, coated tablets, pills, granules, syrups, emulsions, suspensions and solutions, using inert, non-toxic pharmaceutically suitable vehicles or solvents. The therapeutically active compound should in each case be present in a concentration of about 0.5 to 90% by weight of the total mixture, that is to say in amounts which suffice to achieve the dosage range indicated.

The formulations are prepared, for example, by extending the active compounds with solvents and/or vehicles, optionally with the use of emulsifiers and/or dispersing agents, and, for example, when using water as a diluent, organic solvents can optionally be used as auxiliary solvents.

Examples of auxiliaries which may be mentioned are: water, non-toxic organic solvents, such as paraffins (for example petroleum fractions), vegetable oils (for example groundnut oil-sesame oil), alcohols (for example ethyl alcohol and glycerol) and glycols (for example propylene glycol and polyethylene glycol), solid vehicles such as, for example, natural rock powders (for example kaolins, aluminas, talc and chalk), synthetic rock powders (for example highly disperse silica and silicates) and sugars (for example sucrose, lactose and glucose), emulsifiers, such as non-ionic and anionic emulsifiers (for example polyoxyethylene fatty acid esters, polyoxyethylene fatty alcohol ethers, alkylsulphonates and arylsulphonates), dispersing agents (for example lignin, methylcellulose, starch and polyvinylpyrrolidone) and lubricants (for example magnesium stearate, talc, stearic acid and sodium lauryl sulphate).

Administration is effected in the customary manner, preferably orally or parenterally.

In the case of oral use, tablets can, of course, also contain, in addition to the vehicles mentioned, additives such as sodium citrate, calcium carbonate and calcium phosphate, together with various additional substances, such as starch, preferably potato starch, gelatin and the like. Furthermore, lubricants, such as magnesium stearate, sodium lauryl sulphate and talc, can also be used when making tablets. In the case of aqueous suspensions and/or elixirs which are intended for oral use, the active compounds can be mixed with various flavor-improving agents or colorants in addition to the abovementioned auxiliaries.

In the case of parenteral administration, solutions of the active compounds, employing suitable liquid vehicles, can be used. In the case of parenteral use, the fact that the compounds according to the invention are capable of forming salts which are readily soluble in water has proved to be particularly advantageous. These salts are obtained when the compounds according to the invention are combined, in a suitable solvent, with the equimolar amount of a non-toxic inorganic or organic base. Examples which may be mentioned are: sodium hydroxide solution, potassium hydroxide solution, ethanolamine, diethanolamine, triethanolamine, aminotrishydroxymethylmethane, glucosamine and N-methylglucosamine. Salts of these types can also have a greater importance for oral use of the compounds according to the invention since they accelerate or slow down absorption as desired. Apart from the salts already mentioned above, examples which may be mentioned are: magnesium salts, calcium salts, aluminum salts and iron salts.

In general, it has proved advantageous, in the case of parenteral administration, to administer amounts of about 0.05 to 100 mg/kg, preferably about 0.1 to 10 mg/kg of body weight daily to achieve effective results, and in the case of oral administration, the dosage is about 0.1 to 500 mg/kg, preferably 0.5 to 100 mg/kg of body weight daily.

Nevertheless, it can at times be necessary to deviate from the amounts mentioned, and in particular to do so as a function of the body weight of the experimental animal or of the nature of the administration method, but also because of the species of animal and its individual behavior towards the medicament, the nature of the formulation of the medicament and the time or interval over which the administration takes place. Thus it can suffice in some cases to manage with less than the abovementioned minimum amount, while in other cases the upper limit mentioned must be exceeded. Where relatively large amounts are administered, it can be advisable to divide these into several individual administrations over the course of the day.

These statements apply for use of the compounds according to the invention both in veterinary and also in human medicine.

The phosphate compounds of the general formula (III) employed for carrying out the process for preparation according to the invention are known or can be prepared by known methods, (compare I. Shahak et al. Isr. J. Chem. 7, 585 (1969)).

Examples of strong bases for use in carrying out the process variant (a) which may be mentioned are: alkali metal hydrides, such as sodium hydride, potassium hydride and lithium hydride, and alkali metal alcoholates, such as sodium ethylate, potassium ethylate or potassium methylate or alkali metal alkyls, such as methyllithium or butyllithium.

The acetamide derivatives of the general formula (V) employed for carrying out the process variant (c) are known or can be prepared by known methods (compare a) British Patent Specification 715,896 (1954); C.A. 49, 13290d (1955); (b) German Patent Specification 1,142,859 (1960); C.A. 59, 7377c (1963)).

In this process variant (c), acid or basic catalysts are preferably employed, of which examples which may be mentioned are: basic amines, such as dialkylamines, piperidine or pyridine or inorganic acids, in particular hydrochloric acid or condensing agents, such as carboxylic anhydrides.

The alkenoic acids of the general formula (VI) employed according to process variant (d) have not hitherto been disclosed, but can be prepared in a manner known per se by the processes indicated above. The activation of the free carboxyl group, which is advantageous for the reaction with amines, is preferably carried out via the corresponding acid halide, in particular via the corresponding acid chloride, using substances forming halides, such as, for example, thionyl chloride, phosphorus trichloride and phosphorus pentachloride.

In all the processes according to the invention, the customary inert organic solvents can be employed as diluents. These preferably include ethers, such as diethyl ether, glycol ethers, such as glycol dimethyl ether, dioxane, tetrahydrofuran or alcohols, such as methanol, ethanol, propanol, butanol or benzyl alcohol, or sulphoxides, such as dimethyl sulphoxide, bases, such as pyridine, quinoline, picoline or hydrocarbons, such as benzene, toluene or xylene and dimethylformamide.

In the preparation of the alkenoic acids of the general formula (VI), the bases preferably used for hydrolyzing the corresponding esters are: alkali metal hydroxides, such as sodium hydroxide, potassium hydroxide, alkaline earth metal hydroxide, such as barium hydroxide or calcium hydroxide.

In the preparation via the aldehydes of the general formula (II), with $R^4$ equal to hydrogen, with malonic acids of the general formula $R^5$—$CH(COOH)_2$, the condensing agents which are preferably used are: pyridine, substituted pyridine derivatives, such as dialkylaminopyridines, quinoline, isoquinoline, dialkylamines, such as dimethylamine and dibutylamine, pyrrolidine, piperidine and similar nitrogen-containing organic bases.

The following Examples A to G illustrate the preparation of the imidazothiadiazoles of the general formula (VIII) used as starting substances according to the invention (Table 1).

The Examples H to L illustrate the preparation of the carbonyl compounds of the general formula (II) used according to the invention (Table 2).

The examples which then follow illustrate the preparation of the imidazothidiazolealkenamides of the general formula (I) according to the invention (Table 3).

PRACTICAL EXAMPLES

Examples for the preparation of imidazothiadiazoles of the general formula VIII

EXAMPLE A

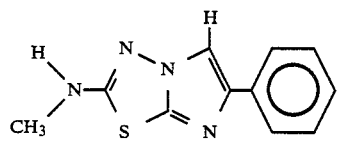

2-Methylamino-6-phenylimidazo[2,1-b]-1,3,4-thiadiazole 18.0 g of 2-bromo-5-amino-1,3,4-thiadiazole (0.1 mol) and 20.0 g of ω-bromoacetophenone (0.1 mol) in 250 ml of dimethylformamide are heated to 100° C. for 4.5 hours. After cooling down to room temperature, 100 ml of ice-water are added and the precipitate is filtered off with suction. After drying, it is taken up in chloroform and, after the addition of ether, recrystallized. The crude 2-bromo-6-phenylimidazo[2,1-b]-1,3,4-thiadiazole is then heated to reflux for 2 hours in 250 ml of ethanol with 25 ml of 30% strength methylamine solution. After cooling down, precipitation is by addition of 200 ml of water, the precipitate is filtered off with suction and recrystallized from chloroform/ether. Yield: 12.6 g (55%) Melting point: 177° C.

EXAMPLE B

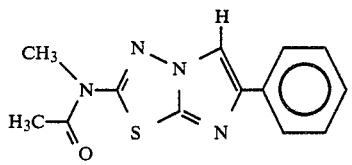

N-acetyl-N-methyl-2-amino-6-phenylimidazo[2,1-b]-1,3,4-thiadiazole 23.0 g of 2-methylamino-6-phenylimidazo[2,1-b]-1,3,4-thiadiazole (0.1 mol) in 200 ml of acetic anhydride are heated to reflux. After cooling down, 200 ml of ether are added, and the precipitate is filtered off with suction and dried. Yield: 25.8 g (99%) Melting point: 280° C.

TABLE 1

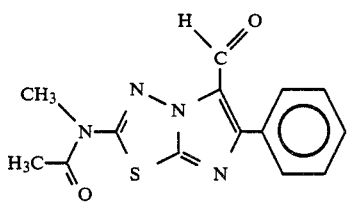
(VIII)

| Example | $R^1$ | $R^2$ | $R^3$ | Melting point | Yield % of theory |
|---|---|---|---|---|---|
| C | H | $nC_3H_7$ | $C_6H_5$ | 174° C. | 87 |
| D | $CH_3CO$ | $nC_3H_7$ | $C_6H_5$ | 160° C. | 73 |
| E | H | $C_2H_5$ | $C_6H_5$ | 162° C. | 80 |
| F | $CH_3CO$ | $C_2H_5$ | $C_6H_5$ | 215° C. | 60 |
| G | H | H | $C_6H_5$ | 192° C. | 90 |

EXAMPLES FOR THE PREPARATION OF CARBONYL COMPOUNDS OF THE GENERAL FORMULA II

EXAMPLE H

N-acetyl-N-methyl-2-amino-6-phenylimidazo[2,1-b]-1,3,4-thiadiazole-5-carbaldehyde 27.2 g of N-acetyl-N-methyl-2-amino-6-phenylimidazo[2,1-b]-1,3,4-thiadiazole (0.1 mol) are added at room temperature to a solution, prepared cold, of 18 ml of phosphorus oxychloride in 300 ml of dry dimethylformamide and heated at 80° C. for 45 minutes. After cooling down, 250 ml of ice-water are added and the precipitate is filtered off with suction and dissolved in chloroform. After drying over sodium sulphate, the solution is evaporated and, after the addition of ether, recrystallized. Yield: 27.0 g (90%) Melting point: 237° C.

TABLE 2

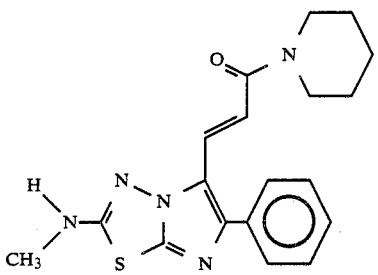

| Example | $R^1$ | $R^2$ | $R^3$ | $R^4$ | Yield % | Melting point |
|---|---|---|---|---|---|---|
| I | $CH_3CO$ | $C_2H_5$ | $C_6H_5$ | H | 91 | 181° C. |
| K | $CH_3CO$ | $nC_3H_7$ | $C_6H_5$ | H | 95 | 183–195° C. |
| L | $=C\diagup\overset{H}{\underset{N(CH_3)_2}{}}$ | | $C_6H_5$ | H | 69 | 159° C. |

EXAMPLES FOR THE PREPARATION OF IMIDAZOTHIADIAZOLEALKENECARBOXAMIDES OF THE GENERAL FORMULA (I)

EXAMPLE 1

N-[β-(2-methylamino-6-phenylimidazo[2,1-b]-1,3,4-thiadiazol-5-yl)-E-propenoyl]piperidine 2.9 g of diethylphosphonoacetic acid piperidide (0.011 mol) are added to 0.33 g of 80% sodium hydride (0.011 mol) (oil removed with petroleum ether) in 100 ml of toluene (anhydrous) and the mixture is heated at 60° C. until evolution of hydrogen is finished. 2.6 g of N-acetyl-N-methyl-2-amino-6-phenylimidazo[2,1-b]-1,3,4-thiadiazole-5-carbaldehyde are added at room temperature and the mixture is stirred at 50° C. for one hour. After cooling down, 20 ml of ethanol are added and, after 30 minutes, 100 ml of water. The organic phase is separated off, the aqueous phase is extracted twice more with chloroform and the organic phases are dried over sodium sulphate. After evaporation, recrystallization is from chloroform/ether. Yield: 2.49 g (68%) Melting point: 264° C.

EXAMPLE 2

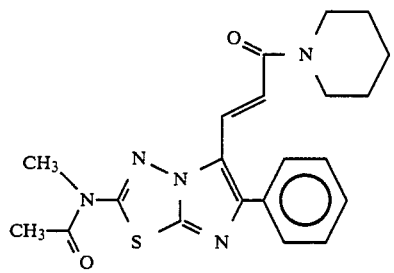

N-[β-(N-acetyl-N-methyl-2-amino-5-phenylimidazo[2,1-b]-1,3,4-thiadiazol-5-yl)-E-propenoyl]-piperidine 3.67 g of N-β-(2-methylamino-6-phenylimidazo[2,1-b]-1,3,4-thiadiazol-5-yl)-E-propenoylpiperidine (0.01 mol) in 50 ml of acetic anhydride are heated to reflux for one hour. After cooling down, 50 ml of ether are added and the precipitate is filtered off with suction. Yield: 2.94 g (72%) Melting point: 209° C.

TABLE 3

| Example No. | $R^1$ | $R^2$ | $R^3$ | $R^4$ | $R^5$ | $NR^6R^7$ | Yield % | Melting point |
|---|---|---|---|---|---|---|---|---|
| 3 | H | $CH_3$ | $C_6H_5$ | H | H | $N(C_2H_2)(C_2H_5)$ | 60 | 236–40° C. |
| 4 | H | $CH_3$ | $C_6H_5$ | H | H | 2-ethylpiperidino | 30 | 204° C. |
| 5 | $CH_3NH$—CO | $CH_3$ | $C_6H_5$ | H | H | $N(C_2H_5)_2$ | 60 | 161° C. |
| 6 | $CH_3$—$SO_2$ | $CH_3$ | $C_6H_5$ | H | H | $N(C_2H_5)_2$ | 50 | 206° C. |
| 7 | H | $nC_3H_7$ | $C_6H_5$ | H | H | $N(C_2H_5)_2$ | 60 | 185° C. |
| 8 | $CH_3CO$ | $nC_3H_7$ | $C_6H_5$ | H | H | $N(C_2H_5)_2$ | 73 | 164° C. |

TABLE 3-continued

[Structure shown at top of table: a compound with substituents R¹, R², R³, R⁴, R⁵, R⁶, R⁷ on a thiosemicarbazone-type scaffold with an amide group]

| Example No. | R¹ | R² | R³ | R⁴ | R⁵ | NR⁶R⁷ | Yield % | Melting point |
|---|---|---|---|---|---|---|---|---|
| 9 | H | nC$_3$H$_7$ | C$_6$H$_5$ | H | H | 2-ethylpiperidinyl | 50 | 222° C. |
| 10 | H | nC$_3$H$_7$ | C$_6$H$_5$ | H | H | piperidinyl | 70 | 262° C. |
| 11 | CH$_3$CO | nC$_3$H$_7$ | C$_6$H$_5$ | H | H | piperidinyl | 20 | 219° C. |
| 12 | H | nC$_3$H$_7$ | C$_6$H$_5$ | H | H | morpholinyl | 50 | 278° C. |
| 13 | CH$_3$CO | nC$_3$H$_7$ | C$_6$H$_5$ | H | H | morpholinyl | 60 | 205° C. |
| 14 | H | C$_2$H$_5$ | C$_6$H$_5$ | H | H | N(C$_2$H$_5$)$_2$ | 66 | 167° C. |
| 15 | H | C$_2$H$_5$ | C$_6$H$_5$ | H | H | piperidinyl | 71 | 232° C. |
| 16 | H | C$_2$H$_5$ | C$_6$H$_5$ | H | H | morpholinyl | 68 | 216° C. |
| 17 | CH$_3$CO | CH$_3$ | C$_6$H$_5$ | H | H | N(C$_2$H$_5$)$_2$ | 64 | 209° C. |
| 18 | C$_6$H$_5$—CO | CH$_3$ | C$_6$H$_5$ | H | H | N(C$_2$H$_5$)$_2$ | 69 | 257° C. |

TABLE 3-continued

[Structure: R¹R²N-C(=S)-N-N= fused bicyclic with R³, bearing -C(R⁴)=C(R⁵)-C(=O)-NR⁶R⁷]

| Example No. | R¹ | R² | R³ | R⁴ | R⁵ | NR⁶R⁷ | Yield % | Melting point |
|---|---|---|---|---|---|---|---|---|
| 19 | $C_2H_5{-}CO$ | $CH_3$ | $C_6H_5$ | H | H | piperidino | 73 | 214° C. |
| 20 | $C_2H_5{-}CO$ | $CH_3$ | $C_6H_5$ | H | H | $N(C_2H_5)_2$ | 80 | 170° C. |
| 21 | $CH_3NH{-}CO$ | $CH_3$ | $C_6H_5$ | H | H | piperidino | 10 | 177° C. |
| 22 | $(CH_3)_2N{-}CO$ | $CH_3$ | $C_6H_5$ | H | H | piperidino | 95 | 160° C. |
| 23 | $CH_3CO$ | $C_2H_5$ | $C_6H_5$ | H | H | $N(C_2H_5)_2$ | 75 | 160° C. |
| 24 | $C_2H_5CO$ | $C_2H_5$ | $C_6H_5$ | H | H | $N(C_2H_5)_2$ | 76 | 187° C. |
| 25 | $C_6H_5{-}CO$ | $C_2H_5$ | $C_6H_5$ | H | H | $N(C_2H_5)_2$ | 70 | 246° C. |
| 26 | $(CH_3)_2N{-}CO$ | $C_2H_5$ | $C_6H_5$ | H | H | $N(C_2H_5)_2$ | 66 | 167° C. |
| 27 | $CH_3NH{-}CO$ | $C_2H_5$ | $C_6H_5$ | H | H | $N(C_2H_5)_2$ | 43 | 197° C. |
| 28 | $(CH_3)_2CHNH{-}CO$ | $C_6H_5$ | $C_6H_5$ | H | H | $N(C_2H_5)_2$ | 84 | 181° C. |
| 29 | $(CH_3)_2CHNH{-}CO$ | $CH_3$ | $C_6H_5$ | H | H | $N(C_2H_5)_2$ | 81 | 207° C. |

TABLE 3-continued

| Example No. | R$^1$ | R$^2$ | R$^3$ | R$^4$ | R$^5$ | $\begin{array}{c}R^6\\ \diagdown N\diagup\\ R^7\end{array}$ | Yield % | Melting point |
|---|---|---|---|---|---|---|---|---|
| 30 | C$_6$H$_5$ | CH$_3$ | C$_6$H$_5$ | H | H | piperidine | 78 | 238° C. |
| 31 | H | H | C$_6$H$_5$ | H | H | 2-ethylpiperidine | 70 | 230° C. |
| 32 | H | H | C$_6$H$_5$ | H | H | piperidine | 75 | 292° C. |
| 33 | H | H | C$_6$H$_5$ | H | H | morpholine | 70 | 208° C. |
| 34 | CH$_3$—C(=O)— | H | C$_6$H$_5$ | H | H | piperidine | 90 | 264° C. |
| 35 | (CH$_3$)$_2$CH—O—C(=O)— | H | C$_6$H$_5$ | H | H | piperidine | 65 | 228° C. |
| 36 | CH$_3$SO$_2$— | H | C$_6$H$_5$ | H | H | piperidine | 90 | 198° C. |
| 37 | C$_6$H$_5$C(=O)— | H | C$_6$H$_5$ | H | H | piperidine | 80 | 241° C. |
| 38 | C$_2$H$_5$—NH—C(=O)— | H | C$_6$H$_5$ | H | H | piperidine | 90 | 190° C. |
| 39 | C$_2$H$_5$—C(=O)— | H | C$_6$H$_5$ | H | H | piperidine | 85 | 231° C. |

TABLE 3-continued
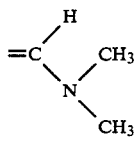
| Example No. | R¹ | R² | R³ | R⁴ | R⁵ | N(R⁶)(R⁷) | Yield % | Melting point |
|---|---|---|---|---|---|---|---|---|
| 40 | =CH-N(CH₃)₂ | | C₆H₅ | H | H | 2-ethylpiperidino | 90 | 182° C. |
| 41 | =CH-N(CH₃)₂ | | C₆H₅ | H | H | piperidino | 92 | 206-8° C. |
| 42 | =CH-N(CH₃)₂ | | C₆H₅ | H | H | morpholino | 90 | 223° C. |
| 43 | =CH-N(CH₃)₂ | | C₆H₅ | H | H | N(C₂H₅)₂ | 96 | 173° C. |
| 44 | =CH-N(CH₃)₂ | | C₆H₅ | H | H | pyrrolidino | 90 | 206° C. |
| 45 | =CH-N(C₂H₅)₂ | | C₆H₅ | H | H | morpholino | 80 | 174° C. |
| 46 | =CH-N(C₂H₅)₂ | | C₆H₅ | H | H | piperidino | 90 | 120° C. |
| 47 | =CH-N(C₂H₅)₂ | | C₆H₅ | H | H | N(C₂H₅)₂ | 85 | 136° C. |

TABLE 3-continued

[Structure: Compound with substituents $R^1, R^2$ on thiourea nitrogen, connected through N-N to a thiazole ring bearing $R^3$, with a vinyl group $R^4, R^5$ leading to a C(=O)N($R^6$)($R^7$) amide]

| Example No. | $R^1$ | $R^2$ | $R^3$ | $R^4$ | $R^5$ | $N(R^6)(R^7)$ | Yield % | Melting point |
|---|---|---|---|---|---|---|---|---|
| 48 | =C(H)(N(C$_2$H$_5$)$_2$) | | C$_6$H$_5$ | H | H | piperidinyl | 90 | 168° C. |
| 49 | =C(CH$_3$)(N(CH$_3$)$_2$) | | C$_6$H$_5$ | H | H | piperidinyl | 70 | 220° C. |
| 50 | =C(CH$_3$)(N(CH$_3$)(CH$_2$—C$_6$H$_5$)) | | C$_6$H$_5$ | H | H | piperidinyl | 60 | 165° C. |
| 51 | =C(CH$_3$)(N(CH$_2$—CH(CH$_3$)$_2$)$_2$) | | C$_6$H$_5$ | H | H | piperidinyl | 70 | 184° C. |
| 52 | =C(CH$_3$)(piperidin-1-yl) | | C$_6$H$_5$ | H | H | piperidinyl | 65 | 170° C. |
| 53 | =C(CH(CH$_3$)$_2$)(piperidin-1-yl) | | C$_6$H$_5$ | H | H | piperidinyl | 90 | 206° C. |
| 54 | =C(N-methyl-azepan-2-ylidene) | | C$_6$H$_5$ | H | H | piperidinyl | 80 | 215° C. |
| 55 | =C(N-methyl-pyrrolidin-2-ylidene) | | C$_6$H$_5$ | H | H | piperidinyl | 60 | 261° C. |

TABLE 3-continued

| Example No. | $R^1$ | $R^2$ | $R^3$ | $R^4$ | $R^5$ | $\begin{array}{c}R^6\\ \diagdown N \diagup \\ R^7\end{array}$ | Yield % | Melting point |
|---|---|---|---|---|---|---|---|---|
| 56 | N-pyrrolinyl-CH$_2$-C$_6$H$_5$ | | C$_6$H$_5$ | H | H | piperidinyl | 50 | 190° C. |
| 57 | =C(C$_2$H$_5$)(N-pyrrolidinyl) | | C$_6$H$_5$ | H | H | piperidinyl | 90 | 228° C. |

It will be appreciated that the instant specification and examples are set forth by way of illustration and not limitation, and that various modifications and changes may be made without departing from the spirit and scope of the present invention.

We claim:

1. An imidazothiadiazolealkenecarboxamide of the formula

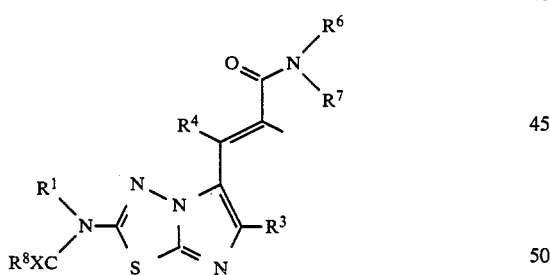

in which

R$^1$ represents hydrogen, phenyl, or phenyl substituted by halogen, trifluoromethyl, alkyl, alkoxy, alkylmercapto or alkylamino, each having 1 to 4 carbon atoms in the alkyl and alkoxy radicals, or by amino, or R$^1$ represents an unsubstituted hydrocarbon radical having up to 12 carbon atoms which is uninterrupted by hetero atoms or interrupted once or twice by O, N, NH, N-alkyl having 1 to 4 C atoms, N-phenyl or N-benzyl, and being unsubstituted or substituted by hydroxyl, alkyl having 1 to 4 C atoms, trifluoromethyl, halogen, phenyl or alkoxycarbonyl having up to 5 C atoms or by dialkylamino, each alkyl radical containing 1 to 4 carbon atoms, the two alkyl radicals being unconnected or forming with the nitrogen atom a 5 to 7-membered ring, containing no further heteroatoms or said 5 to 7 membered ring containing a further heteroatom from the group comprising O, NH or N-alkyl having 1 to 4 C atoms, and which is unsubstituted or substituted by halogen or alkyl having 1 to 4 C atoms, R$^8$ has the meaning indicated for R$^1$ and being identical to or different from R$^1$, and X representing oxygen, sulphur or the radical NR$^9$R$^{10}$, R$^9$ and R$^{10}$ being identical or different and representing hydrogen, phenyl, benzyl or alkyl having 1 to 6 carbon atoms, the alkyl and phenyl radicals being unsubstituted or substituted by halogen or alkoxy having 1 to 4 carbon atoms; or represents the radical SO$_n$R$^{11}$, n denoting 1 or 2 and R$^{11}$ having the meaning indicated for R$^1$ and being identical to or different from R$^1$, or R$^1$ and R$^2$ together represent a group of the formula =C(R$^{12}$) (Y—R$^{13}$), Y representing oxygen, sulphur, NH or N-alkyl having 1 to 4 C atoms, and R$^{12}$ and R$^{13}$ each having the meaning indicated for R$^1$ and being identical to or different from R$^1$, R$^{12}$ and R$^{13}$ being unconnected or R$^{12}$ and R$^{13}$ connected together to form, with inclusion of =C—Y, a 5 to 7-membered ring having no further heteroatom or contains a further heteroatom from the group comprising O, S, NH or N-alkyl having 1 to 4 C atoms, R$^3$ has the meaning indicated for R$^1$ and is identical to or different from R$^1$ or represents unsubstituted phenyl, furyl, thienyl, pyrimidyl or pyridyl, or phenyl, furyl, thienyl, pyrimidyl or pyridyl substituted by 1, 2 or 3 identical or different substituents from the group comprising halogen, nitro, trifluoromethyl, phenyl, alkyl, alkoxy, dialkylamino or SO$_n$-alkyl, wherein n is 0, 1 or 2, the alkyl and alkoxy radicals mentioned each containing 1 to 4 carbon atoms, R⁴ represents hydrogen, trifluoromethyl or alkyl, R⁵ represents hydrogen, cyano, halogen, nitro, alkyl, SO$_n$-alkyl or CXR⁸, the alkyl radicals mentioned containing 1 to 4 carbon atoms and n, X and R⁸ having the meaning indicated above, and R⁶ and R⁷ each have the meaning indicated for R¹ and are identical to or different from R¹ or, R⁶ and R⁷ being unconnected or connected with the nitrogen atom form a 5 or 7-membered saturated or unsaturated ring, the ring containing no further heteroatoms or contains 1 or 2 further heteroatoms from the group comprising oxygen, sulphur or nitrogen, the nitrogen being unsubstituted or substituted by hydrogen, alkyl having 1 to 4 carbon atoms, phenyl or benzyl and this 5 to 7-membered ring being unsubstituted or substituted by 1, 2 or 3 identical or different substituents from the group comprising halogen, trifluoromethyl, phenyl, benzyl, alkyl, alkoxy, alkoxyalkyl, hydroxyalkyl or alkoxycarbonyl, the alkyl and alkoxy radicals mentioned each containing 1 to 4 C atoms, this 5 to 7-membered ring being uncondensed or condensed with an aromatic ring having 6 to 10 carbon atoms, which in turn is unsubstituted or substituted by halogen, trifluoromethyl, nitroalkyl or alkoxy each having 1 to 4 C atoms, or a pharmaceutically acceptable acid addition salt thereof.

2. A compound or salt according to claim 1, in which

R¹ represents hydrogen, phenyl or a hydrocarbon radical having up to 6 carbon atoms, which is uninterrupted by heteroatoms or is interrupted once by oxygen, NH, N-alkyl having 1 to 4 C atoms or N-benzyl and which is unsubstituted or substituted by halogen, R² represents hydrogen or the radical CXR⁸, R⁸ having the meaning indicated for R¹ and being identical to or different from R¹ and X representing oxygen or the radical NR⁹R¹⁰, R⁹ and R¹⁰ being identical or different and each having the meaning indicated for R¹, or R¹ and R² together represent a group of the formula =C(R¹²) (Y—R¹³), Y representing the radical N-alkyl having 1 to 4 C atoms and R¹² and R¹³ being identical or different and each having the meaning indicated for R¹ and being identical to or different from R¹, R³ has the meaning indicated for R¹ and is identical to or different from R¹ or represents unsubstituted phenyl, furyl, thienyl, pyrimidyl or pyridyl, or phenyl, furyl, thienyl, pyrimidyl or pyridyl substituted by one or two identical or different substituents from the group comprising halogen, nitro, trifluoromethyl, phenyl, alkyl, alkoxy, dialkylamino or SO$_n$-alkyl, wherein n is 0 or 2, the alkyl and alkoxy radicals mentioned each containing 1 to 4 carbon atoms, R⁴ and R⁵ are identical or different and represent hydrogen or alkyl having 1 to 4 carbon atoms and R⁶ and R⁷ have the meaning indicated for R¹ and are identical to or different from R¹ or connected together with the nitrogen atom to form a 5 to 7-membere ring which is uninterrupted by further heteroatoms or interrupted by one oxygen or nitrogen atom, the nitrogen optionally being unsubstituted or substituted by hydrogen, alkyl having 1 to 4 carbon atoms or benzyl and this 5 to 7-membered ring being unsubstituted or substituted by one or two identical or different substituents from the group comprising halogen, benzyl, trifluoromethyl, alkyl or alkoxy each having 1 to 4 carbon atoms, this ring being uncondensed or condensed with an aromatic ring having 6 or 10 C atoms.

3. A compound according to claim 1, wherein such compound is N-[β-(2-N-Methyl-N-methyl-carbamoyl-6-phenylimidazo [2,1-b]-1,3,4-thiadiazol-5-yl)-propenoyl]-diethylamine of the formula

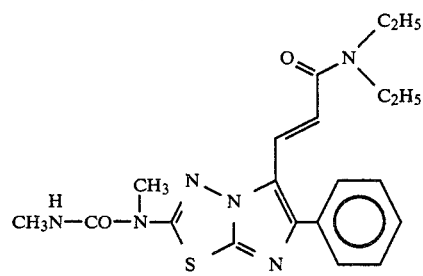

4. A compound according to claim 1, wherein such compound is N-[β-(Dimethylamino-methylen-2-amino-6-phenylimidazo[2,1-b]-1,3,4-thiadiazol-5-yl)-propenoyl]-piperidine of the formula

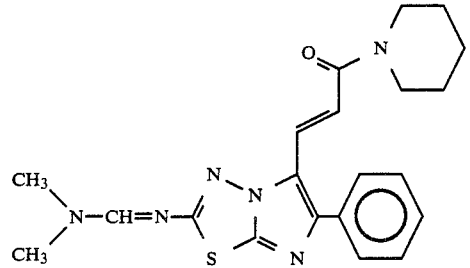

5. A compound according to claim 1, wherein such compound is N-[β-(Dimethylamino-methylen-2-amino-6-phenylimidazo[2,1-b]-1,3,4-thiadiazol-5-yl)-propenoyl]-diethylamine of the formula

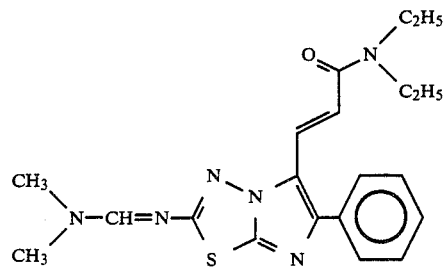

6. A compound according to claim 1, wherein such compound is N-[β-(Diethylamino-methylen-2-amino-6-phenylimidazo[2,1-b]-1,3,4-thiadiazol-5-yl)-propenoyl]-morpholine of the formula 7. A compound according to claim 1, wherein such compound is N-[β-(Diethylamino-methylen-2-amino-6-phenylimidazo[2,1-b]-1,3,4-thiadiazol-5-yl)-propenoyl]-piperidine of the formula
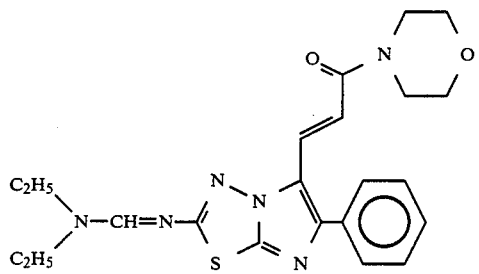
8. A compound according to claim 1, wherein such compound is N-[β-(α-Pyrrolidino-propenyliden-2-amino-6-(phenylimidazo[2,1-b]-1,3,4-thiadiazol-5-yl)-propenoyl]-piperidine of the formula
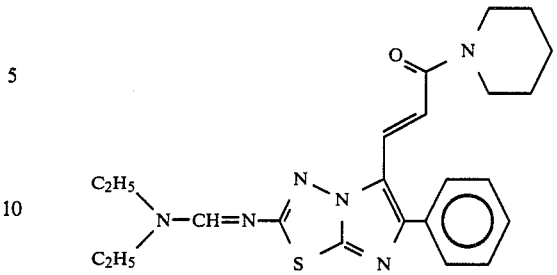
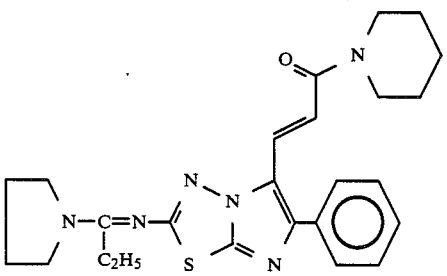
* * * * *